United States Patent [19]

Tassin, Jr.

[11] Patent Number: 4,509,534

[45] Date of Patent: Apr. 9, 1985

[54] BLOOD WITHDRAWAL APPARATUS AND METHOD OF USING SAME

[76] Inventor: Myron J. Tassin, Jr., 732 Dalzell St., Shreveport, La. 71104

[21] Appl. No.: 388,419

[22] Filed: Jun. 14, 1982

[51] Int. Cl.³ .............................................. A61M 5/14
[52] U.S. Cl. .................................. 128/764; 128/766; 604/44
[58] Field of Search ........................ 128/760, 763–766; 604/43, 44, 86, 164, 165, 169

[56] References Cited

U.S. PATENT DOCUMENTS

| 2,854,027 | 9/1958 | Kaiser et al. | 137/625.41 |
|---|---|---|---|
| 3,459,183 | 8/1969 | Ring et al. | 128/763 |
| 3,565,074 | 2/1971 | Foti | 604/164 |
| 3,720,210 | 3/1973 | Diettrich | 604/164 X |
| 3,817,240 | 6/1974 | Ayres | 128/764 |
| 3,874,367 | 4/1975 | Ayres | 128/766 |
| 3,875,938 | 4/1975 | Mellor | 604/169 X |
| 3,996,923 | 2/1976 | Guerra | 128/2 F |
| 4,106,491 | 8/1978 | Guerra | 128/2 F |
| 4,186,752 | 2/1980 | Guerra | 128/766 |
| 4,230,128 | 10/1980 | Aramayo | 128/763 |
| 4,252,117 | 2/1981 | Sheehan | 128/214 R |
| 4,319,582 | 3/1982 | Eldridge | 128/766 |
| 4,326,541 | 4/1982 | Eckels | 128/766 |

FOREIGN PATENT DOCUMENTS 2203858  5/1973  Fed. Rep. of Germany .

OTHER PUBLICATIONS

B-D Vacutainer Evacuated Blood Collection Tube Brochure 9/76-P10162(BZ), Becton-Dickinson & Co., Rutherford, N.J. 07070.
Deseret Angiocath Intravenous Catheter Placement Units, Form B-4349B (2-78), Deseret Company, Sandy, Utah 84070.
Flashball Device-Travenol Laboratories, Inc. of Deerfield, IL, No. 8-1-49-555 7/81, Code 2C0001, "Solution Administration Set".

Primary Examiner—Edward M. Coven
Attorney, Agent, or Firm—Pravel, Gambrell, Hewitt & Kimball

[57] ABSTRACT

A new improved blood withdrawal apparatus and method for using same wherein the apparatus includes a test tube housing for receiving a blood sample test tube, a test tube penetration assembly with the test tube housing for penetrating the blood sample test tube, a valve mechanism in flow communication with the test tube penetration assembly and the test tube housing for regulating the flow of blood to the test tube penetration assembly, and a connection assembly with the valve mechanism for connecting the valve mechanism in flow communication with an intravenous catheter positioned in the vein of the subject.

16 Claims, 6 Drawing Figures

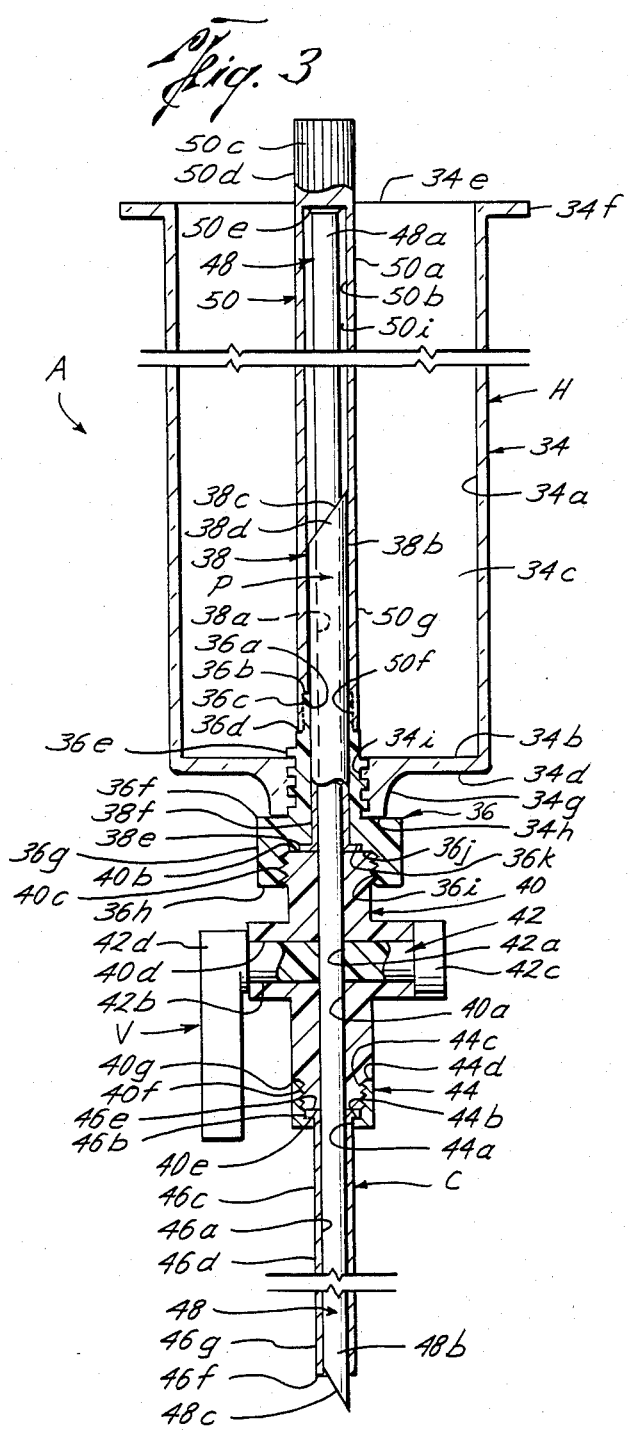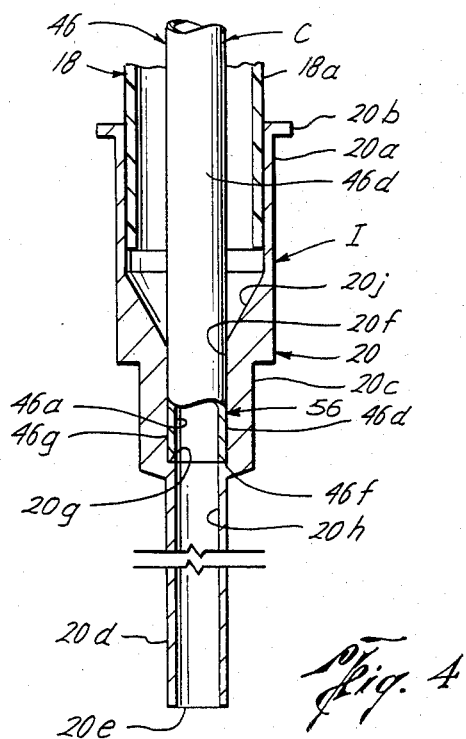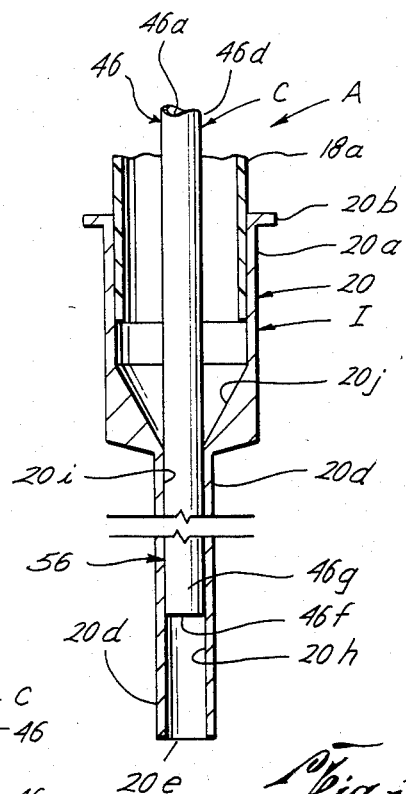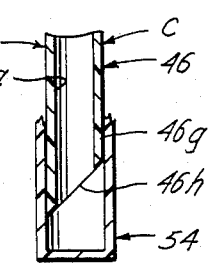

BLOOD WITHDRAWAL APPARATUS AND METHOD OF USING SAME

FIELD OF THE INVENTION

The field of this invention relates generally to medical devices, particularly of the type utilized in withdrawing blood from a subject.

DESCRIPTION OF PRIOR ART

It has long been known that blood may be withdrawn from a subject by means of a conventional needle/syringe arrangement whereby the needle is inserted into the vein of the subject and the syringe is actuated in such a manner that blood is withdrawn into the chamber of the syringe. This technique is often used when an isolated sample of the blood is needed. However, in situations where a subject has been exposed to a greater trauma, typically a variety of intraveneous catheters are positioned at various venous positions throughout the subject's body during hospitalization. Typically such catheters are used for connecting the subject with intravenous fluids that are capable of sustaining life while the subject is recovering from the trauma or chronic illness that has been experienced.

Typically, while a subject is receiving such intravenous fluids, the sampling of blood is often required. This, so far as known, typically requires the insertion of additional catheters and/or needles in other venous locations throughout the subject's body, a procedure which is not only painful to the subject but also can pose some difficulty in those patients where veins are not readily found.

Prior art devices include such as those akin to the "Vacutainer" brand evacuated blood collection tube as manufactured by Becton-Dickinson of Rutherford, N.J. The "Vacutainer" system utilized a needle-housing assembly, wherein the needle is inserted through the subject's epidermal layers and positioned within the vein. A test tube is secured in a test tube housing of the "Vacutainer" system. After the needle is positioned in the vein of the subject and the test tube collecting the blood sample is properly positioned within the holder, a blood sample may thereafter be collected. After the collection of the original sample, the test tube may be removed from the housing. Upon removal of the test tube, an elastomeric sheath closes an eyelet of a penetrating needle that is within the test tube housing of the "Vacutainer" system. The elastomeric sheath covers the eyelet after the test tube is removed and the eyelet may once again be exposed for blood flow upon reinsertion of a new blood sample test tube into the "Vacutainer" apparatus.

So far as known, no system is currently available that permits utilization of an intravenous fluid catheter to be also utilized as a point of entry into the subject's veins for the withdrawal of blood therefrom.

SUMMARY OF THE INVENTION

The present invention relates to a new and improved blood withdrawal apparatus and method of using same, wherein the apparatus includes a test tube housing, test tube penetration assembly for penetrating the test tube that is adapted to be mounted with the housing, a valve mechanism in flow communication with the penetration assembly for regulating flow of blood to the test tube assembly and connection members with the valve mechanism for connecting the valve members in flow communication with the intravenous catheter positioned in the vein of the subject.

BRIEF DESCRIPTION OF THE DRAWINGS

FIG. 3 is an enlarged, elevational, sectional view of the blood withdrawal apparatus of the present invention;

FIG. 3A is an enlarged, sectional view of an alternative embodiment of the connecting needle of the blood withdrawal apparatus of the present invention;

FIG. 4 depicts a first embodiment in an elevational, sectional view, showing the proper positioning of the connecting needle within the intravenous catheter; and, FIG. 5 depicts a second embodiment in an elevational, sectional view, showing the connecting needle as properly disposed within an intravenous catheter.

DESCRIPTION OF THE PREFERRED EMBODIMENT

Figure 1:
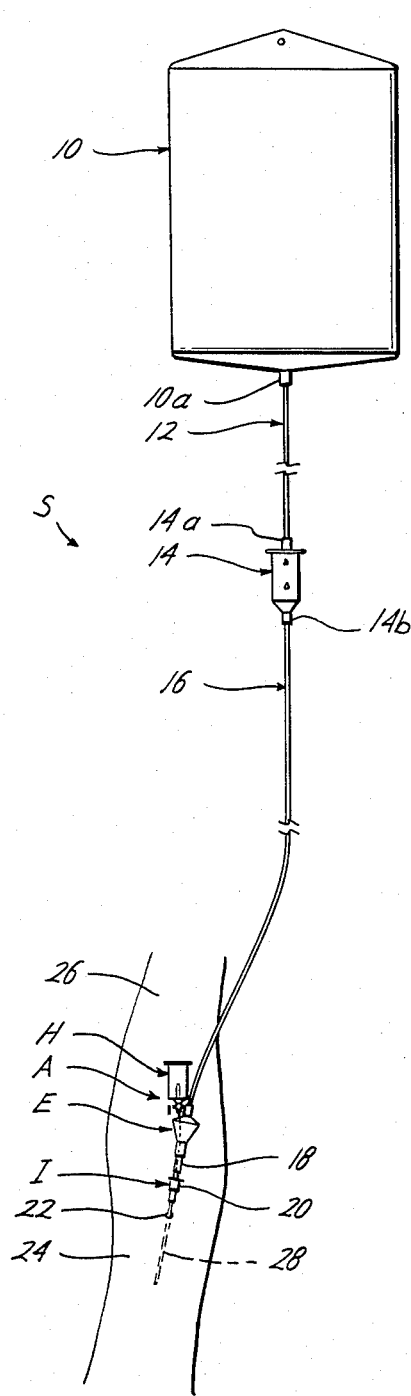
FIG. 1 schematically depicts an intravenous fluid system incorporating the blood withdrawal apparatus of the present invention.

The present invention relates to a new and improved blood withdrawal apparatus designated generally in the drawings by the letter A, that is adapted to be used with an intravenous fluid system S. The blood withdrawal apparatus A includes generally a test tube housing H for receiving a blood sample test tube T therein, a test tube penetration means P for penetrating the blood sample test tube T, valve means V in flow communication with the tube penetration means P and mounted with test tube housing H for regulating flow of blood to the test tube penetration means P, and connection means C with the valve means V for connecting the valve means V in flow communication with the intravenous catheter I positioned in the vein of the subject.

The blood withdrawal system A is adapted to be used with an intravenous fluid system S. The intravenous fluid system S includes generally an intravenous fluid container 10 that is adapted to receive intravenous fluid therein. The intravenous fluid container 10 is formed having a fluid outlet 10a adjacent its lower end, with the outlet 10a adapted to be in flow communication with the intravenous fluid contained within the intravenous fluid container 10. The outlet 10a is in flow communication with intravenous fluid tubing 12 which communicates with the inlet 14a of drip chamber 14. The drip chamber 14 includes an outlet 14b at its lower end which is in flow communication with intravenous tubing 16. The drip chamber 14, as is known, indicates the flow rate of intravenous fluid from the intravenous fluid container 10 to the intravenous tubing 16 for proper rate regulation thereof. The intravenous tubing 16 is connected with intravenous tubing 18 by entry device E, discussed more fully hereinbelow.

The intravenous tubing 18 is adapted to be mounted with intravenous catheter I, with the intravenous tubing 18 being formed having a stepped collar 18a which is adapted to be received in the enlarged mounting portion 20a of the catheter 20 of the intravenous catheter I at its lower end 18b. The catheter 20 is further formed having an annular lip 20b adjacent its upper end, and a reduced portion 20c below the enlarged mounting portion 20a, with a suitable flexible venous insert 20d formed with the lower end of the reduced portion 20c. The flexible venous insert 20d is adapted to be mounted within an opening 22 formed in the epidermal layers 24 of the subject 26, thereinto the vein 28 of the subject 26, such that the flexible venous insert 20d may be inserted through the opening 22 and thereinto the vein 28 of the subject 26, as is known. A bore 20h (FIGS. 4,5) is formed within the catheter 20 so that fluid may flow through the catheter 20 between the annular lip 20b and the lower end 20e of the flexible venous insert 20d. As such, intravenous fluid in intravenous fluid container 10 thus may flow from the intravenous container 10, through intravenous tubing 12, drip chamber 14, intravenous tubing 16, entry device E, intravenous tubing 18, and intravenous catheter I thereinto the vein 28 of the subject 26 for normal intravenous fluid treatments with the intravenous fluid system S.

Figure 2:
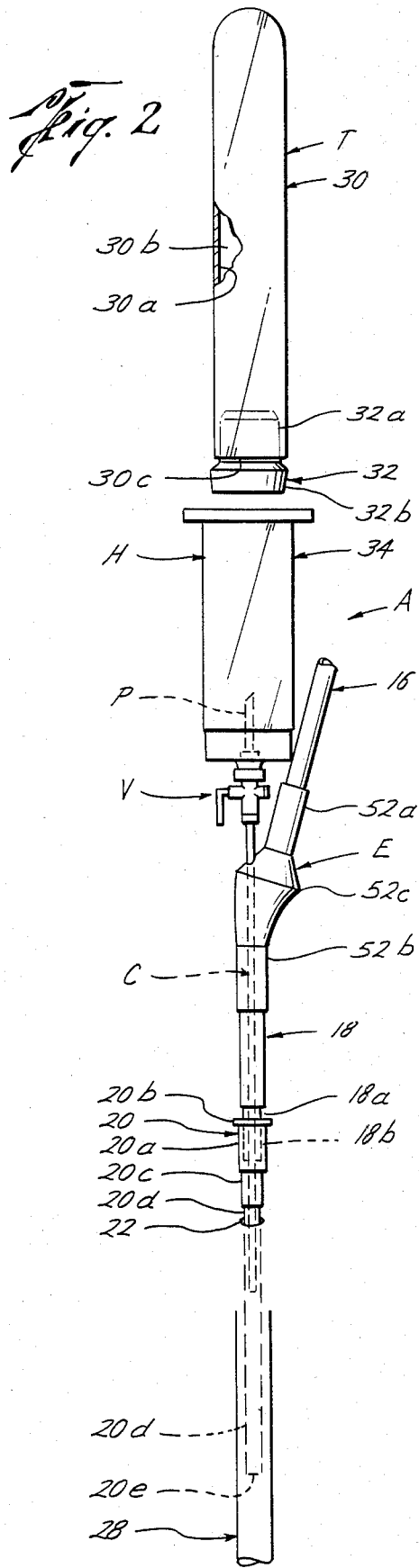
FIG. 2 depicts an elevational view of the blood withdrawal apparatus of the present invention as utilized with a portion of the intravenous fluid system.

The blood withdrawal apparatus A is adapted to be used with the intravenous fluid system S and mountable therewith adjacent to the entry device E as discussed more fully hereinbelow. The blood withdrawal apparatus A is used for collecting in a blood sample test tube T samples of blood withdrawn through the intravenous catheter I positioned in the vein 28 of the subject 26 having intravenous infusions when using the intravenous fluid system S. The blood withdrawal apparatus A is adapted to use a blood sample test tube T (FIG. 2). The blood sample test tube T includes a test tube 30 that may be formed of glass, plastic or any other suitable material that may be sterilized, as desired. The test tube 30 is formed having an inner wall surface 30a which defines chamber 30b. A suitable enclosure 32 is mounted adjacent open end 30c of the test tube 30. The end closure 32 is preferably formed having a neck portion 32a which is adapted to be inserted into the test tube 30 and in sealable engagement with the inner wall surface 30a. An enlarged mounting portion 32b is formed adjacent the neck portion 32a at the enclosure 32 for proper mounting of the test tube 30 with the test tube housing A, as discussed more fully hereinbelow. It is preferred that the chamber 30b of the test tube 30 contain a vacuum for proper use thereof in the system S of the present invention. The end closure 32 is adapted to be formed of a material that may be punctured by a needle or the like, permit sealing therewith, and upon removal thereof, reseal the opening, such as a latex or any other suitable materials.

The blood withdrawal apparatus A includes a test tube housing H for receiving the blood sample test tube T therein. The test tube housing H includes housing 34 having an inner annular surface 34a and an inner radial surface 34b. The inner annular surface 34a and inner radial surface 34b define the test tube receiving chamber 34c formed within the housing 34. Preferably the inner radial surface 34b is formed adjacent the closed end 34d of the housing 34, while open end 34e is adjacent the radial lip 34f formed at the upper end of the housing 34 (FIG. 3). The test tube housing H further includes a mounting flange 36 formed adjacent to the closed end 34d of the housing 34. The mounting flange 36 is preferably formed having a bore 36a an upper shoulder 36b, a threaded portion 36c adjacent to the upper shoulder 36b, a radial lip 36d adjacent to threaded portion 36c, a threaded portion 36e, a radial surface 36f, an outer annular surface 36g, a lower shoulder 36h formed adjacent to outer annular surface 36g, an inner threaded portion 36i, an inner radial surface 36j, and a penetrating needle flange retaining surface 36k adjacent the bore 36a. Preferably, the housing 34 is formed having a neck portion 34g formed adjacent the closed end 34d and inner radial surface 34b, preferably centrally thereof and extending downwardly from the closed end 34d, as viewed in FIG. 3. An end surface 34h is formed adjacent to the lower end of the neck portion 34g, with a suitable threaded bore 34i formed adjacent to the end surface 34h. Preferably, the threaded bore 34i extends between the inner radial surface 34b and end surface 34h and is adapted to receive compatably formed threaded portion 36e of the mounting flange 36. When the mounting flange 36 is properly positioned and mounted with the housing 34, the threaded portion 36e is in threaded engagement with the threaded bore 34i and the end surface 34h engages the radial surface 36f of the mounting flange 36.

The blood withdrawal apparatus A of the present invention further includes test tube penetration means P within the test tube receiving chamber 34c of the housing 34 of the test tube housing H. The test tube penetration means P is capable of penetrating the end closure 32 of the blood sample test tube T when the blood sample test tube T is properly positioned with the test tube receiving chamber 34c of the housing 34. The test tube penetration means P includes a penetrating needle 38 which is adapted to be mounted with the mounting flange 36. The penetrating needle 38 includes a bore 38a, an outer annular surface 38b, a beveled penetrating end 38c formed adjacent its upper end 38d, and a radial mounting flange 38e formed adjacent its lower end 38f. The penetrating needle 38 is adapted to be positioned with the mounting flange 36 such that the outer annular surface of the penetrating needle 38 is snugly secured within the bore 36a of the mounting flange 36, with the radial mounting flange 38e of the penetrating needle 38 being compatably disposed within a similarly configured penetrating needle flange retaining surface 36k of the mounting flange 36. Alternatively, the mounting flange 36 may be secured by molding the housing 34 around the mounting flange 36, such as by plastic molding techniques, by way of example.

The blood withdrawal apparatus A further includes valve means V in flow communication with the test tube penetrating means P. The valve means V is mounted with the test tube housing H for regulating the flow of blood to the test tube penetration means P from the vein 28 of the subject 26, as discussed more fully hereinbelow. The valve means V includes a valve housing 40 and a valve element 42. The valve housing 40 is mountable with and beneath the closed end 34d of the housing 34 of the test tube housing H. More particularly, the valve housing 40 is preferably formed having a bore 40a, an upper end surface 40b, and an exterior threaded portion 40c adjacent to upper end surface 40b. The valve housing 40 further includes a valve element chamber 40d formed centrally thereof and a lower end surface 40e having threaded portion 40f adjacent thereto, with radial lip 40b formed adjacent the threaded portion 40f.

The valve housing 40 is adapted to receive a valve element 42 therein. The valve element 42 is movable between a closed position wherein blood may not flow into the test tube penetration P and an open position where blood may flow into the test tube penetration means P. As shown in FIG. 3, the valve element 42 may be formed having a bore 42a, a cylindrical element 42b adapted to be disposed within the valve element chamber 40d of the valve housing 40, an end cap 42c, and a handle 42d. As such, the end cap 42c properly locates the cylindrical element 42b within the valve element chamber 40d. The handle 42d permits selective operator movement of the valve element 42 between the open and closed position. As best seen in FIG. 3, when the bore 42a of valve element 42 is aligned with the bore 40a of the valve housing 40, the valve means V is in an open position while when the bore 42a is misaligned such that bores 40a, 42a do not communicate with one another, then the valve means V is in a closed position. It should be appreciated that the valve element 42-valve housing 40 structure as depicted in FIG. 3 is of a "stopcock" type arrangement; however, other types of valve configurations such as ball valves, by way of example but not by way of limitation, may alternatively be used as the valve means V of the blood withdrawal apparatus A of the present invention.

The valve housing 40 of the valve means V is threadedly mounted with the mounting flange 36 by threaded interaction between the exterior threaded portion 40c of valve housing 40 and inner threaded portion 36i of mounting flange 36. When proper threaded engagement occurs therebetween, the upper end surface 40b engages the inner radial surface 36j of the mounting flange 36 and secures the penetrating needle 38 within the penetrating flange retaining surface 36k while engaging the radial mounting flange 38e of the penetrating needle 38. Alternatively, if a molding procedure as identified hereinabove, were to be utilized, the costs of manufacture would be reduced but the costs of replacing the penetrating needle 38 would increase. Thus, should it be desired that the penetrating needle 38 be replaced, the valve housing 40 need only be unthreaded from the mounting flange 36, the penetrating needle 38 removed from the bore 36a of the mounting flange and a new penetrating needle 38 reinserted into the bore 38a of the mounting flange 36. The radial mounting flange 38e is in contact with the penetrating needle flange retaining surface 36k of the mounting flange 36. The valve housing 40 thereafter is threadedly affixed with the mounting flange 36.

The valve means V of the blood withdrawal apparatus A further includes a connecting needle mounting cap 44 that is adapted to threadedly engage the valve means V. Preferably, the connecting needle mounting cap 44 includes a bore 44a, an inner radial surface 44b, an inner annular threaded surface 44c and an end shoulder 44d.

The connection means C of the blood withdrawal apparatus A of the present invention is with the valve means V for connection with the valve means V in flow communication with the intravenous catheter I positioned within the vein 28 of the subject 26. The connection means C includes a connecting needle 46 mountable with the valve means V and in flow communication with the catheter 20. Preferably, the connecting needle 46 is formed having a bore 46a therethrough and a radial mounting flange 46b at its upper end 46c to be received in the connecting needle mounting cap 44. More specifically, preferably the radial mounting flange 46b of the connecting needle 46 has an upper surface 46e which is adapted to engage the inner radial surface 44b of the connecting needle mounting cap 44, with the outer annular surface 46d of the connecting needle 46 engaging the bore 44a of the connecting needle mounting cap 44. Threaded action between the inner annular threaded surface 44c of the connecting needle mounting cap 44 and the threaded portion 40f of the valve housing 40 permits the connecting needle 46 to be removably connected with the valve housing 40 when end shoulder 44d engages radial lip 40g and end surface 46e of the radial mounting flange 46b abuts the lower end surface 40e of the valve housing 40. An alternative molding procedure, such as molded plastic by way of example, could also be employed to secure the connecting needle 46 with the valve means V. Thus, the connecting needle 46 extends through the bore 44a of the connecting needle mounting cap 44 and downwardly therefrom as viewed in FIG. 3.

It is preferred that the connecting needle 46 be of a blunt tip 46f adjacent its lower end of 46g. When the connecting needle 46 is of a blunt tip 46f configuration, it is preferred that a connecting needle 46 be formed of a suitable high strength stainless steel. Alternatively, it is contemplated that the connecting needle 46 may include a beveled tip 46h (FIG. 3A) adjacent the lower end 46g. With a beveled tip 46h, the connecting needle 46 is preferably formed of a suitable high strength plastic material, as discussed more fully hereinbelow. Thus, the connecting needle 46 may be removably mounted with the valve means V by means of the connecting needle mounting needle cap 44.

The blood withdrawal apparatus A thus includes bore 38a of penetrating needle 38, bore 40a of valve housing 40, bore 42a of valve element 42, and bore 46a of the connecting needle 46 that are adapted to be in substantial axial-alignment when the valve means V is in an open position as shown in FIG. 3. Preferably, all such bores 38a, 40a, 42a, and 46a are substantially the same diameter.

The blood withdrawal appartus A further includes an inner cannula 48 that is adapted to be positioned in the axially aligned bores 38a, 40a, 42a, 46a for permitting ease of insertion of the connection means C into the entry device E, discussed more fully hereinbelow. The inner cannula 48 is preferably of an elongate, solid, rod-shaped configuration having an upper end 48a and a lower end 48b. Preferably the lower end 48b is formed into a beveled surface 48c while the upper end 48a has a cannula cover 50 therewith. The lower end 48b of the inner cannula 48 may be of other suitable configurations than the beveled surface 48c, as desired. Preferably, the cannula cover 50 includes an outer annular surface 50a, an inner annular surface 50b, a gripping surface 50c formed adjacent the upper end 50d thereof and an inner radial surface 50e formed adjacent the inner annular surface 50b, adjacent the upper end 50d. Preferably, the upper end 48a of inner cannula 48 is adapted to be affixed with the cannula cover 50 adjacent the inner radial surface 50e of cannula cover 50. It should be noted that the diameter of threaded bore 34i is larger than the diameter of the cannula cover 50, such that the assembly thereof may be affixed to the test tube housing H by inserting the upper end 50d of the cannula cover 50 through the bore 34i of the housing 34 with the valve means V already affixed prior to threaded engagement between threads 34e, 36e. An inner threaded portion 50f is formed on the inner annular surface 50b adjacent the lower end 50g and is adapted to threadedly engage the threaded portion 36c of mounting flange 36. As such, the inner annular surface 50b and inner radial surface 50e define an inner chamber 50i formed within the cannula cover 50. Inner chamber 50i, is adapted to receive the test tube penetration means P therein for housing same. The inner cannula 48 is adapted to be inserted within the aligned axial bores 38a, 40a, 42a, 46a prior to utilization of the blood withdrawal apparatus A. As such, the cannula cover 50 is of such a dimension that when such is threadedly secured with the mounting flange 36 adjacent threaded portion 36c, the inner cannula 48 is positioned within such axially aligned bores such that the beveled surface 48c of the inner cannula 48 protrudes just beyond the blunt tip 46f of the connecting needle 46. Thus, the cannula cover 50 not only houses the penetrating needle 38 of the test tube penetration means P, but also insures that the beveled surface 48c of the inner cannula 48 is properly positioned adjacent the blunt tip 46f of the connecting needle 46. Unthreading of the cannula cover 50 from the mounting flange 36 permits the inner cannula 48 to be withdrawn from within the aligned axial bores.

The blood withdrawal apparatus A is adapted to be mounted with an entry device E, as best seen in FIG. 2. Preferably the entry device E includes an entry housing 52 having an inlet end 52a adapted to be in flow communication with intravenous tubing 16. An outlet end 52b of entry housing 52 is adapted to be in flow communication with intravenous tubing 18 and a bulb portion 52c is disposed between the inlet end 52a and outlet end 52b. Preferably, the bulb portion 52c, having an inner chamber (not shown), permits flow communication between the inlet end 52a and outlet end 52b of the entry housing 52. It is preferred that the bulb portion 52c be formed of latex or other suitable material capable of being penetrated by a suitable needle, such as the beveled surface 48c of inner cannula 48 and blunt tip 46f of connecting needle 46, while properly maintaining a sealable relation. Alternatively, a capped hub (not shown) may be located on or near catheter mounting portion 20a through which a connecting needle 46 could gain temporary entry and thereafter be re-capped for maintaining sterility. Thereafter, the connecting needle 46 may be removed from the bulb portion 52c of the entry housing 52 and the entry opening formed by the penetration of the connecting needle 46, thereafter be sealed by the surrounding material of the bulb portion 52c. Such an entry housing 52 is currently commercially available and is marketed by Travenol Laboratories of Deerfield, Ill. and is known as a "Flashball" device ("Flashball" is a registered trademark of Travenol Laboratories).

As such, the beveled surface 48c of the inner cannula 48 adjacent the to blunt tip 46f of the connecting needle 46 permits ease of insertion thereinto the entry housing 52 such that the beveled surface 48c and the blunt tip 46f are within the chamber (not shown) within the bulb portion 52c of the entry housing 52. Thereafter, the gripping surface 50c of the cannula cover 50 is rotated to result in unthreading action between the cannula cover 50 and the mounting flange 36, whereinafter the inner cannula 48 may be withdrawn and removed from within the aligned axial bores 46a, 40a, 42a, 38a. The connecting needle 46 may thereafter be further passed through the outlet end 52b of the entry housing 52 into the intravenous tubing 18, thereinto the intravenous catheter I. In the event that the connecting needle 46 is not of a blunt tip 46f, but rather a beveled tip 46h (FIG. 3A), the need for an inner cannula 48 and cannula cover 50 may be eliminated. The beveled tip 46h should be capable of penetrating the bulb portion 52c of the entry housing 52 in such a fashion that there is no disruption to the material of the bulb portion 52c that would destroy its sealable characteristics and/or cause a portion of such material to become lodged within the bore 46a of the connecting needle 46 or cause a portion of the catheter 20 to become dislodged into the vein 28 of subject 26. A needle cover 54 is depicted in FIG. 3A as protecting the connecting needle 46 and its beveled tip 46h from damage or contamination. The needle cover 54 would necessarily be removed prior to insertion of the connecting needle 46 into the entry device D.

As best seen in FIG. 4, the inserting of the connecting needle 46 into the intravenous catheter I preferably terminates at sealable engagement means, designated generally as 56, and formed with the intravenous catheter I. As shown in FIG. 4, the sealable engagement means 56 may include a suitable inner annular surface 20f and an adjacent radial surface 20g that permits insertion of the connecting needle 46 into the catheter 20 such that the blunt tip 46f of the connecting needle 46 engages radial surface 20g while the outer annular surface 46d of the connecting needle 46 engages the inner annular surface 20f. Thus, as shown in FIG. 4, the sealable engagement means 56 includes the inner annular surface 20f and radial surface 20g formed with the catheter 20. The bore 46a of the connecting needle 46 corresponds with that of the bore 20h of the catheter 20 of the intravenous catheter I and such bores 46a, 20h are in substantial axial alignment therewith. The tapered surface 20j enhances ease of proper placement of the connecting needle 46 in the catheter 20.

Alternatively, as shown in FIG. 5, the connecting needle 46 of the connection means C may be sealably positioned within the bore 20h of the catheter 20 adjacent sealing bore surface 20i of the catheter 20. Sealing bore surface 20i is adapted to engage the outer annular surface 46d of the connecting needle 46 adjacent its lower end 46g. Thus, the sealable engagement means 56 may also include the sealing bore surface 20i formed with the catheter 20 of the intravenous catheter I. Thus, the sealable engagement means 56 is formed with the intravenous catheter I for insuring positive sealing between the connection means C and the intravenous catheter I. As in FIG. 4, the tapered surface 20j of the catheter 20 of FIG. 5 enhances ease of proper placement of the connecting needle 46 in the catheter 20, but is not totally necessary in either the catheters 20 of FIGS. 4 or 5, and may alternatively be used with known types of catheters.

In the use and operation of the blood withdrawal apparatus A of the present invention for collecting in a blood sample test tube T the blood withdrawn through an intravenous catheter I positioned in a vein 28 of a subject 26 receiving intravenous fluid with an intravenous fluid system S, the blood withdrawal apparatus A is of the configuration shown in FIG. 3 prior to insertion into the entry device E. As such, the beveled surface 48c of the inner cannula 48 and blunt tip 46f of the connecting needle 46 are inserted into the bulb portion 52c of the entry housing 52. Thereafter, the gripping surfaces 50c of the cannula cover 50 are grasped and rotated for unthreading the cannula cover 50 from the mounting flange 36. Upon unthreaded rotation thereof, the inner cannula 48 may be retracted and removed from the aligned axial bores 46a, 40a, 42a, 38a. The valve means V is then moved such that it is closed resulting in no fluid flow between and through the bores 40a, 42a. Thereafter, the connecting needle 46 may be passed through the remainder of the bulb portion 52c and outlet end 52b of the entry housing 52, into intravenous tubing 18, and thereinto intravenous catheter 1. Thereafter the connecting needle 46 of the connection means C is sealably positioned in the intravenous catheter by means of the sealable engagement means 56 so as to prevent the flow of intravenous fluid into the intravenous catheter and permitting the withdrawal of blood from the vein 28 of the subject 26 through the intravenous catheter I by utilizing the blood withdrawal apparatus A. Thus, it will be appreciated by utilization of the sealable engagement means 56, the flow of intravenous fluid from the intravenous fluid system S is interrupted and stopped by proper sealing of the lower end 46g of the blunt tip 46f of the connecting needle 46 within the catheter 20. Thereafter, a blood sample test tube T is positioned about the open end 34e of the housing 34 and inserted into the test tube receiving chamber 34c such that the beveled penetrating end 38c of the penetrating needle 38 may penetrate the end closure 32 of the test tube 30 in a sealable fashion with the enlarged mounting portion 32b of the enclosure 32 being in proximal engagement with the inner annular surface 34a of the housing 34. When properly positioned, the test tube 30 is mounted within the test tube receiving chamber 34c such that the end closure 32 is adjacent to the inner radial surface 34b of the closed end 34d of the housing 34. In such a position, the beveled penetrating end 38c extends well into the chamber 30b within the test tube 30 which preferably contains a vacuum. Thereafter, it is necessary that any entrained intravenous fluid in proximity to the properly positioned lower end 46g of the connecting needle 46 be purged from the system S. Thus, a small amount of blood, for example, one cubic centimeter (cc), be withdrawn including such entrained intravenous fluid, if any. Such is withdrawn by opening the valve means V to permit the withdrawal of such a small quantity of blood from the vein 28 of the subject 26 by the flow of blood from the vein 28 therethrough the blood withdrawal apparatus A thereinto the the blood sample test tube T. Thereafter, the valve means V must be closed and the blood sample test tube T removed from the test tube housing H and discarded. Thereafter, a new blood sample test tube T must be replaced in the test tube housing H with the test tube penetration means P penetrating the end enclosure 32 of the test tube 30 as before. Thereafter, the valve means V may be reopened permitting the withdrawal of blood by flow thereof from the vein 28 therethrough the intravenous catheter I, through the connection means C, valve means V, test tube penetration P, thereinto the blood sample test tube T for collecting samples of blood of the subject 26 in the blood sample test tube T. Thereafter, the valve means V preferably should be closed and the blood filled blood sample test tube T removed from the blood withdrawal apparatus A of the present invention. Thereafter, the procedure of mounting new blood sample test tubes T, with the test tube housing H, opening the valve means V to permit filling of the blood sample test tubes T closing the valve means V and thereafter removing the filled blood sample tubes from the test tube housing H may be accomplished as many times as necessary without the need of catheters or needles in addition to that used for typical intravenous fluid systems S. Upon completion of filling all the necessary blood sample test tubes T, the connecting needle 46 of the connection means C is withdrawn from the intravenous catheter I and entry device E (with the valve means V closed) to permit the substantially simultaneous reintroduction of intravenous fluid into the intravenous catheter I, after completion of blood withdrawal activities without adjustment of the flow regulation.

In the past, it has been unacceptable to draw blood for analysis from the same extremity receiving an intravenous fluid, because blood in that extremity was thought to contain a higher concentration of intravenous fluid than blood that has been mixed thoroughly with the intravenous solution and located elsewhere in the cardio-vascular system. Presuming that the subject 26 has a cardiac output capable of sustaining life, it has been documented by *Stewart Hamilton Method Of Cardiac Output Determination* that after injection of intravenous fluid into a vein 28, the intravenous solution is carried to the heart and pumped into the aorta within 15 seconds (assuming a human subject 26). This solution is considered to be throughly mixed after it returns to the veins 28 of the subject 26. Thus, theoretically, after waiting 15 seconds, the blood drawn through the intravenous catheter I will represent blood in all other portions in the venous side of the cardio-vascular system. This should be true only after the intravenous solution that lies just beyond the lower end of 46g of the connecting needle 46 and the intravenous catheter I is cleared. It is accordingly thus recommended that the first purging operations of the entrained intravenous fluid, if any, be withdrawn and discarded.

Furthermore, it should be noted that blood will not clot in the lower end 20e of the catheter 20 during the 15 second waiting period under normal circumstances. In subjects 26 having hyper-coagulability, if a clot does begin to form it will be drawn into the blood sample test tube T, containing the first purged portions, which will be discarded. On the other hand, when the connecting needle 46 is withdrawn from the intravenous catheter I, the blood located at the lower end 20e of the catheter 20 will be washed into the vein 28 by the intravenous, fluid as its flow returns immediately. It should be noted that the connecting needle 46 preferably is of the blunt tip 46f configuration because if the angle of the bevel were sharp enough to penetrate the bulk portion 52c of the entry housing 52 without leaving an opening in it after withdrawing the connecting needle 46, the connecting needle 46 may be sharp enough to scratch the material within the intravenous catheter I, resulting in a foreign embolus in the circulatory system. Thus, to counteract this result the connecting needle 46 is preferably blunt and penetration of the bulk portion 52c of the entry housing 52 is accomplished with the beveled surface 48c of the inner cannula 48. Alternatively, the inner cannula 48 could be totally eliminated if the female ends of the intravenous catheter I were constructed of a high density, scratch resistant plastic containing a funnel portion 20j which would enhance self sealing of the connecting needle 46 within the intravenous catheter I, whether in the form of FIG. 4 or FIG. 5, or if a connecting needle as depicted in FIG. 3A were used.

Furthermore in using the blood withdrawal apparatus A of the present invention, it is anticipated that both the penetrating needle 38 and connecting needle 46 will be pre-packaged in sterile containers. Once such needles 38,46 are removed from the sterile containers, they will be held securely by appropriate needle covers, such as needle cover 54 in order to maintain sterility and permit proper attachment with the blood withdrawal apparatus A. Alternatively, the test tube penetration means P, valve means V and connection means C may be preassembled and ready to mount onto the test tube housing H. In either instance, everything except the test tube housing H must be sterile. Thereafter the bowl portion 52c of the entry housing 52 will be swabbed with isopropyl alcohol or iodophor in traditional fashions. The connecting needle 46 thereafter is inserted into the bowl portion 52c, with the bowl portion 52c being properly supported so as the pressure of insertion does not disrupt the intravenous catheter's insertion site in the vein of the subject 26.

Thus, the blood withdrawal apparatus A of the present invention and the method of using same provides a new and improved apparatus and method that is designed to eliminate the pain of mutiple veni-punctures typically required for prior art blood sampling techniques. The subject 26 will be spared the pain of such multiple veni-punctures and other risks of prior art blood sampling techniques may be diminished. Furthermore, future intravenous insertion sites will not have been destroyed by subsequent veni-punctures required for prior art blood withdrawal apparatus.

The foregoing disclosure and description of the invention are illustrative and explanatory thereof, and various changes in the size, shape and materials, as well as in the details of the illustrated construction may be made without departing from the spirit of the invention.

I claim:

1. A blood withdrawal apparatus adapted to be mounted in flow communication with an intravenous catheter for collecting in a blood sample test tube samples of blood withdrawn through the intravenous catheter and an entry device, the intravenous catheter positioned in a vein of a subject receiving intravenous fluid and the entry device in flow communication with the intravenous fluid and the intravenous catheter, comprising:

a test tube housing formed having a test tube receiving chamber for receiving the blood sample test tube therein, said test tube housing having an open end and a closed end;

test tube penetration means within said test tube receiving chamber for penetrating the blood sample test tube when the blood sample test tube is properly positioned with said test tube receiving chamber;

valve means in flow communication with said test tube penetration means and mounted with said test tube housing for regulating the flow of blood to said test tube penetration means from the vein of the subject;

a connecting needle having a bore therethrough, said connecting needle having an upper end mounted with said valve means and said connecting needle formed having a blunt surface adjacent its lower end, said connecting needle being in flow communication with said valve means;

said test tube penetration means, said valve means, and said connecting needle are formed having bores that are axially aligned when said valve means is in an open position; and, an inner cannula removably mounted substantially within said axially aligned bores formed in said test tube penetration means, said valve means, and said connecting needle for permitting ease of insertion of said connecting needle solely into the entry device, whereupon said inner cannula is removed for exposing said blunt surface on said lower end of said connecting needle.

2. The blood withdrawal apparatus of claim 1, wherein said valve means further includes:

a valve housing mounted with and beneath said closed end of said test tube housing; and, a valve element mounted within said valve housing, said valve element being movable between a closed position wherein blood may not flow into said test tube penetration means and an open position where blood may flow into said test tube penetration means.

3. The blood withdrawal apparatus of claim 1, wherein:

the test tube housing is formed having a mounting flange adjacent said closed end thereof, said mounting flange being threadedly connected to said valve means.

4. The blood withdrawal apparatus of claim 3, wherein:

said mounting flange is formed having a bore and a penetrating needle flange retaining surface adjacent said threaded connection within said mounting flange and adjacent said valve means; and, said test tube penetration means includes a penetration needle mounted with said bore of said mounting flange and adjacent said penetrating needle flange retaining surface formed in said mounting flange, said penetration needle extending through said bore in said mounting flange into said test tube receiving chamber.

5. The blood withdrawal apparatus of claim 4, wherein:

said penetrating needle is formed having a radial mounting flange adjacent its lower end, said lower end being mounted adjacent said penetrating needle flange retaining surface; and, said penetrating needle formed having a beveled penetrating end adjacent its upper end.

6. The blood withdrawal apparatus of claim 1, wherein:

said inner cannula is of an elongate rod-shaped configuration having an upper end and a lower end, said lower end formed into a beveled surface and said upper end having a cannula cover therewith, said cannula cover cooperating with said test tube housing for insuring the proper positioning of said inner cannula within said axially aligned bores for said beveled surface to protrude from said connection means at the lower end thereof as needed.

7. The blood withdrawal apparatus of claim 6, wherein said cannula cover is formed having an inner chamber receiving said test tube penetration means therein for housing same.

8. The blood withdrawal apparatus of claim 6, wherein said cannula cover is removably mounted with said test tube housing adjacent said closed end thereof.

9. A blood withdrawal apparatus including an intravenous catheter for collecting samples of blood withdrawn through the catheter, comprising:

an intravenous catheter positioned in fluid communication with the interior of the vein of a subject;

a blood sample test tube;

a test tube housing having a test tube receiving chamber for receiving said blood sample test tube therein, said test tube housing having an open end and a closed end;

test tube penetration means associated with said test tube receiving chamber for penetrating the blood sample test tube when the blood sample test tube is properly positioned with respect to said test tube receiving chamber;

valve means in fluid communication with said test tube penetration means and mounted adjacent said test tube housing for regulating the flow of blood to said test tube penetration means from the vein of the subject;

a removable connecting needle having a first and second ends in fluid communication with said valve means for permitting blood to flow from the vein of the subject to said valve means;

a mounting cap associated with said valve means to maintain said first end of the connecting needle in operable relation thereto;

said connecting needle having a radial mounting flange on its first end to cooperate with said mounting cap such that said connecting needle may be removably mounted adjacent said valve means; and, the second end of said connecting needle and said intravenous catheter forming a fluid tight seal to prevent flow of intravenous fluid into the vein of the subject.

10. The blood withdrawal apparatus of claim 9, further including:

an entry device in fluid communication with the intravenous catheter positioned in the vein of the subject and the intravenous fluid therein; and, wherein said second end of the connecting needle has a beveled portion which penetrates said entry device and forms a seal between said connecting needle and the intravenous catheter to permit the withdrawal of samples of blood through the catheter without the incursion of intravenous fluid.

11. A blood withdrawal apparatus in flow communication with an intravenous catheter for collecting in a blood sample test tube samples of blood withdrawn through the intravenous catheter and an entry device, the intravenous catheter positioned in a vein of a subject receiving intravenous fluid and the entry device in flow communication with the intravenous fluid and the intravenous catheter, comprising:

an intravenous catheter;

a test tube housing formed having a test tube receiving chamber for receiving the blood sample test tube therein, said test tube housing having an open end and a closed end;

test tube penetration means with said test tube receiving chamber for penetrating the blood sample test tube when the blood sample test tube is properly positioned with said test tube receiving chamber;

valve means in flow communication with said test tube penetration means and mounted with said test tube housing for regulating the flow of blood to said test tube penetration means from the vein of the subject;

a connecting needle having a bore therethrough, said connecting needle having an upper end mounted with said valve means and said connecting needle formed having a blunt surface adjacent to its lower end, said connecting needle being in flow communication with said valve means;

said test tube penetration means, said valve means and said connecting needle are formed having bores that are axially aligned when said valve means is in an open position;

an inner cannula removably mounted substantially within said axially aligned bores formed in said test tube penetration means, said valve means, and said connecting needle for permitting ease of insertion of said connecting needle solely into the entry device, whereupon said inner cannula is removed for exposing said blunt surface on said lower end of said connecting needle; and said connecting needle sealably engages the intravenous catheter for insuring positive sealing between said connecting needle and the intravenous catheter, thereby preventing flow of intravenous fluids into the vein of the subject.

12. A method for collecting in a blood sample test tube samples of blood withdrawn through an intravenous catheter positioned in a vein of a subject receiving intravenous fluid, comprising the steps of:

inserting a connecting needle of a blood withdrawal apparatus into an entry device in flow communication with an intravenous catheter;

inserting the connecting needle through the entry device to said intravenous catheter positioned in the vein; and, sealably positioning the connecting needle in said intravenous catheter so as to prevent the flow of intravenous fluid into said intravenous catheter and permit the withdrawal of blood from the vein of the subject through said intravenous catheter by utilizing the blood withdrawal apparatus.

13. The method of claim 12, further including the steps of:

mounting an inner cannula substantially within aligned bores of a penetrating means, a valve means, and said connecting needle of the blood withdrawal apparatus prior to said inserting into the entry device for enhancing the ease of said inserting; and, removing said inner cannula from within said aligned bores of the blood withdrawal apparatus after said inserting into said entry device and prior to said insertion into the intravenous catheter.

14. The method of claim 12, further including the steps of:

securing a blood sample test tube with a test tube housing of the blood withdrawal apparatus;

purging any entrained intravenous fluid in said intravenous catheter by opening a valve assembly with the blood withdrawal apparatus to permit the withdrawal of a small quantity of blood from the vein of the subject by the flow of the blood from the vein through said intravenous catheter, through the connecting needle thereinto the blood sample test tube;

closing the valve assembly;

removing the blood sample test tube from the blood withdrawal apparatus;

placing a new blood sample test tube with the blood withdrawal apparatus; and reopening the valve assembly of the blood withdrawal apparatus to permit the flow of blood from said intravenous catheter to the blood sample test tube for collecting samples of blood from the subject.

15. The method of claim 14, further including the steps of:

reclosing the valve assembly of the blood withdrawal apparatus; and, removing the blood filled blood sample test tube from the blood withdrawal apparatus.

16. The method of claim 15, further including the step of:

withdrawing said connecting needle from the intravenous catheter and the entry device after said reclosing to permit the reintroduction of intravenous fluid into said intravenous catheter after completion of blood withdrawal activities.

* * * * *